United States Patent [19]
Huffman et al.

[11] Patent Number: 6,025,500
[45] Date of Patent: Feb. 15, 2000

[54] STEREOSELECTIVE PROCESS FOR ENALAPRIL

[75] Inventors: Mark A. Huffman, Edgewater; Paul J. Reider, Westfield; Carl Leblond, Somerset; Yongkui Sun, Bridgewater, all of N.J.

[73] Assignee: Merck & Co., Ltd., Rahway, N.J.

[21] Appl. No.: 09/397,949

[22] Filed: Sep. 17, 1999

Related U.S. Application Data

[60] Provisional application No. 60/101,458, Sep. 23, 1998.

[51] Int. Cl.$^7$ .................................................. C07D 207/08
[52] U.S. Cl. ............................................................. 548/533
[58] Field of Search ............................................... 548/533

[56] References Cited

U.S. PATENT DOCUMENTS

| | | | |
|---|---|---|---|
| 5,319,098 | 6/1994 | Burbaum et al. | 548/533 |
| 5,473,081 | 12/1995 | Kobayashi et al. | 548/533 |
| 5,670,655 | 9/1997 | Qin et al. | 548/533 |
| 5,707,991 | 1/1998 | Capet et al. | 514/235.5 |
| 5,898,076 | 4/1999 | Giselbrecht et al. | 548/533 |
| 5,962,696 | 10/1999 | Tanner et al. | 548/533 |
| 5,977,380 | 11/1999 | Yang et al. | 548/533 |

OTHER PUBLICATIONS

Blacklock et al, "Synthesis of Semisynthetic Dipeptides Using N–Carboxyanhydrides and Chiral Induction on raney Nickel", J. Org. Chem., 1988, 53, 836–844.

*Primary Examiner*—Deborah C. Lambkin
*Attorney, Agent, or Firm*—Valerie J. Camara; Mark R. Daniel

[57] ABSTRACT

The invention relates to an improved stereoselective heterogenous catalytic reductive amination between ethyl 2-oxo-4-phenylbutyrate and alanylproline using hydrogen, a catalyst and one or more additives to produce the ACE inhibitor, enalapril.

22 Claims, No Drawings

STEREOSELECTIVE PROCESS FOR ENALAPRIL

Provisional Appln No. 60/101,458 Sep. 23, 1998.

FIELD OF THE INVENTION

The invention relates to an improved stereoselective synthesis of enalapril, an ACE inhibitor useful in treating hypertension and heart failure.

BACKGROUND OF THE INVENTION

Enalapril is an ACE inhibitor useful in treating hypertension and heart failure. It is currently marketed in the United States under the trademark VASOTEC (enalapril maleate). It is disclosed and claimed in U.S. Pat. No. 4,374,829.

U.S. Pat. Nos. 4,374,829, 4,472,380 and 4,510,083 disclose methods useful in the preparation of enalapril. The large-scale synthesis of enalapril (1) involves a key diastereoselective reductive amination reaction between the α-ketoester (2) and the dipeptide, alanylproline (3), catalyzed by Raney-Nickel (Ra-Ni). [Blacklock, T. J.; Shuman, R. F.; Butcher, J. W.; Shearin, W. E. Jr.; Budavari, J.; Grenda, V. J.; J. Org. Chem. 1988, 53, 836–844.] The initially reported conditions gave a diastereomer ratio of 6.7:1. Over the past decade, this ratio has been improved to 11:1 using traditional optimization techniques, primarily with the Ra-Ni catalyst. The best ratio achieved with a catalyst other than Ra-Ni was 1.5:1 using palladium on carbon or $IrO_2$.

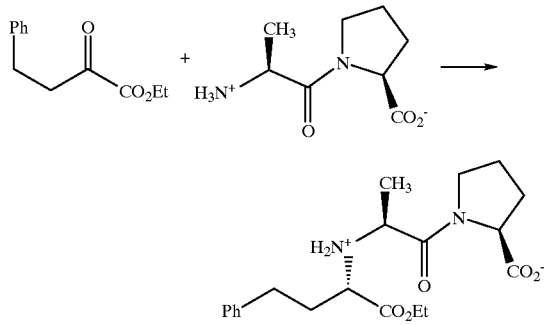

SUMMARY OF THE INVENTION

The invention relates to a heterogeneous catalytic reductive amination between the α-ketoester, ethyl 2-oxo-4-phenylbutyrate (2) and the dipeptide, alanylproline (3) using hydrogen, a catalyst and one or more additives. A multidimensional screening method was employed to determine the optimal parameters for obtaining the desired stereoselectivity and yield.

DETAILED DESCRIPTION OF THE INVENTION

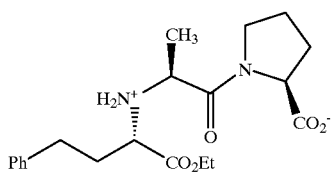

comprising reacting a dipeptide

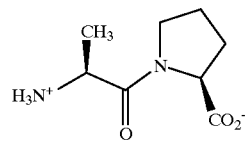

in ethanol, powdered sieves, one or more additives, a catalyst, with an α-ketoester

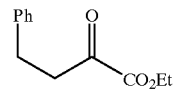

under hydrogen, while stirring, to produce the enalapril.

The process as recited above wherein the catalyst is Ra-Ni, $Pt/Al_2O_3$, and $Pd/Al_2O_3$.

The process as recited above wherein the additives are selected from: amino acid derivatives, carbohydrates, salts, organic acids, and Lewis acids.

The process as recited above wherein one of the additives is a salt such as LiF, NaF, KF, CsF, LiCl, NaCl, KCl, LiBr, NaBr, KBr, NaI, tetraalkylammonium bromides, alkyl is defined as $C_1$–$C_6$ alkyl.

The process as recited above wherein one of the additives is an organic acid such as acetic acid, propionic acid, trifluoroacetic acid, citric acid, lactic acid, ascorbic acid, pyroglutamic acid, diphenylacetic acid, tartaric acid, indole-3-acetic acid, nicotinic acid, nipecotic acid, and picolinic acid.

The process as recited above wherein one of the additives is a Lewis acid such as lanthanum (III) triflate and titanium (IV) chloride.

The process as recited above wherein one of the additives is an amino acid derivative such as: naturally occurring D- and L-amino acids and their esters, N-protected with protecting groups, including acetyl, t-butylcarbamoyl, toluenesulfonyl, phthaloyl.

The process as recited above wherein one of the additives is a carbohydrate such as: D-fructose, L-fructose, D-fucose, L-fucose, D-galactose, L-galactose, D-glucose, L-glucose, D-arabinose, L-arabinose, D-lyxose and L-lyxose.

The process as recited above wherein two additives are used.

The process as recited above wherein the first additive is an organic acid. The process as recited above wherein one of the additives is an organic acid such as acetic acid, propionic acid, trifluoroacetic acid, citric acid, lactic acid, ascorbic acid, pyroglutamic acid, diphenylacetic acid, tartaric acid, indole-3-acetic acid, nicotinic acid, nipecotic acid, and picolinic acid.

The process as recited above wherein the catalyst is Ra-Ni.

The process as recited above wherein the second additive is a salt. The process as recited above wherein the second additive is a salt selected from: LiF, NaF, KF, CsF, LiCl, NaCl, KCl, LiBr, NaBr, KBr, NaI, tetraalkylammonium bromides, wherein alkyl is defined as $C_1$–$C_6$ alkyl.

The process as recited above wherein the two additives are: acetic acid (HOAc) and potassium fluoride (KF), or acetic acid (HOAc) and cesium fluoride (CsF).

The process as recited above wherein about 2 psia to about 100 psia of hydrogen is used.

The process wherein as recited above the reaction temperature is about 0° C. to about 40° C.

The process as recited above wherein about 2 psia to about 54 psia of hydrogen is used.

The process wherein as recited above the reaction temperature is about 15° C. to about 30° C.

The process as recited above wherein the catalyst is Pt/Al₂O₃.

The process as recited above wherein the second additive is a salt.

The process as recited above wherein the second additive is a salt selected from: LiF, NaF, KF, CsF, LiCl, NaCl, KCl, LiBr, NaBr, KBr, NaI, tetraalkylammonium bromides, wherein alkyl is defined as $C_1$–$C_6$ alkyl.

The process as recited above wherein the two additives are: acetic acid (HOAc) and sodium bromide (NaBr).

The process as recited above wherein about 2 psia to about 100 psia of hydrogen is used.

The process wherein as recited above the reaction temperature is about 0° C. to about 40° C.

The process as recited above wherein about 2 psia to about 54 psia of hydrogen is used.

The process wherein as recited above the reaction temperature is about 15° C. to about 30° C.

General Multidimensional Screening Method

The method used was a broad, rapid, two- and three-dimensional screening of heterogeneous catalysts with various additives, either singly or in combination with a second additive. Experiments were performed in a hydrogenation reactor in which up to 18 reactions in vials are stirred in a single vessel under one atm of hydrogen. Reaction set-up was speeded by slurrying the common reagents for a set of reactions and distributing by autopipet. Yield and diastereomer ratio were determined by HPLC.

Representative screening procedure: Alanylproline (1.395 g, 7.5 mmol) and powdered 3A sieves (2.88 g) were suspended in a mixture of absolute ethanol (11.25 mL) and acetic acid (3.75 mL). To the suspension was then added 2-oxo-4-phenylbutyrate (1.56 ml, 8.25 mmol). From the rapidly stirring suspension, 1.3 mL portions were removed by autopipet and transferred into 8 mL vials which had previously been charged with LiF (13 mg, 26 mg, 52 mg) or KF (29 mg, 58 mg, 116 mg). Some of the vials had also been previously charged with 10 mg of 5% platinum on alumina; the remainder were charged with 100 mg of ethanol-wet Raney-Nickel after receiving the reagent slurry. The vials, equipped with magnetic stir bars and needle-pierced septum caps, were placed in a glass pressure vessel. After vacuum/nitrogen purging, the mixtures were stirred under one atm hydrogen at ambient temperature for 21 h. Samples from each vial were diluted 1000X, filtered and assayed by HPLC using an autosampler.

The first set of reactions was a screen of catalysts in ethanol without additives (Table 1). Based on these results, Ra-Ni, Pt/Al₂O₃, and Pd/Al₂O₃ were selected for their superior stereoselectivity or yield, and Pd/C was also included in further experiments. In these and subsequent experiments, overall yield was primarily limited by chemoselectivity toward reductive amination vs. ketone reduction.

TABLE 1

Initial Catalyst Screen

| Catalyst | SSS: RSS | assay yield (SSS + RSS) | Catalyst | SSS:RSS | assay yield (SSS + RSS) |
|---|---|---|---|---|---|
| Raney-Ni | 11:1 | 74 | Pd/C | 1.4:1 | 50 |
| PtO₂ | 1.5:1 | 23 | Pd/Al₂O₃ | 1.6:1 | 70 |
| Pt/C | 1.1:1 | 10 | Pd(OH)₂/C | 1.5:1 | 63 |
| Pt/Al₂O₃ | 2.8:1 | 14 | Pd(S)/C | 1.6:1 | 43 |
| Pt(S)/C | 1.1:1 | 8 | Pd/BaSO₄ | 1.4:1 | 57 |

TABLE 1-continued

Initial Catalyst Screen

| Catalyst | SSS: RSS | assay yield (SSS + RSS) | Catalyst | SSS:RSS | assay yield (SSS + RSS) |
|---|---|---|---|---|---|
| Rh/C | 1:1.2 | 13 | Pd/CaCO₃ | 1.9:1 | 42 |
| Rh/Al₂O₃ | 1.6:1 | 4 | | | |

Several hundred reactions were then run with these four catalysts and one or two additives, in most cases with the additives initially at 10 wt % vs. Ala-Pro. Additives were chosen from a number of classes, both chiral and achiral, including amino acid derivatives, carbohydrates, salts, organic acids, and Lewis acids.

A favorable finding was that with Pt/Al₂O₃, a modest improvement in stereoselectivity occurred with several additives including some carbohydrates and some organic acids, such as pyroglutamic acid, citric acid, and acetic acid. The acetic acid charge was optimized to 25% of the solvent by volume, giving a 4.6:1 SSS:RSS ratio and substantially improved chemoselectivity. Subsequently some salts were found to have a modest but reproducible effect on this Pt/Al₂O₃ in 25% AcOH reaction. Selected examples are shown in Table 2. The combination of NaBr and 25% AcOH in ethanol raised the Pt/Al₂O₃ catalyst performance from a 14% yield and 2.8:1 stereoselectivity to 68% yield and 6.4:1 ratio, a stereoselectivity approaching the 6.7:1 ratio initially reported for Ra-Ni.

TABLE 2

Salt Effects on Pt/Al₂O₃ Reaction in Ethanol/Acetic Acid

| salt | equiv. | SSS:RSS | assay yield (SSS + RSS) |
|---|---|---|---|
| none | | 4.6:1 | 58 |
| LiCl | 4.8 | 6.4:1 | 50 |
| NaCl | 1.8 | 4.9:1 | 62 |
| NaBr | 2.8 | 6.4:1 | 68 |
| LiF | 4.0 | 4.3:1 | 66 |
| KF | 4.0 | 4.0:1 | 11 |
| KF | 1.0 | 3.8:1 | 24 |

A combined screen of salts with other additives and catalysts revealed another valuable combination: Ra-Ni, acetic acid, and KF. The initial hit at 25% AcOH in ethanol and 4 eq. KF gave a 17:1 ratio of SSS to RSS. In optimizing this lead, the ratio of AcOH to KF turned out to be important, but if varied together the quantity of both additives could be reduced while maintaining selectivity. The optimized conditions use 1.25 mol eq. AcOH and 1.05 eq. KF (vs. Ala-Pro) at ambient temperature and 14 psia hydrogen. The product is isolated as enalapril maleate by selective crystallization of the SSS diastereomer with maleic acid. The increased diastereoselectivity (17:1 vs. 11:1) leads to a significant isolated yield improvement in this high-volume, high-value drug.

This discovery has revealed that unlike the acetic acid/salt results for Pt/Al₂O₃, with Ra-Ni, thus far, neither additive has a beneficial effect alone, and in fact, KF without AcOH inhibits the reaction. Also, the effect requires the specific, unique combination of Ra-Ni catalyst, AcOH and KF. With the exception of exchanging CsF for KF, a change in catalyst or either additive removes any benefit. For example, adding KF to the combination of AcOH and Pt/Al₂O₃ depresses yield and selectivity (Table 2). This leads to the conclusion that only experiments that simultaneously vary more than one factor would have discovered these reaction conditions. A more traditional method of optimizing one variable at a time would only find combinations in which each change alone provides a benefit.

The result of this multidimensional screening effort was a process improvement which involves the addition of two inexpensive reagents and which significantly improves reaction selectivity and yield. The value of simultaneously varying multiple parameters was demonstrated, and this approach may be fruitful when applied to any of the factors which can affect a reaction's outcome.

EXAMPLE

Enalapril Maleate

Raney-Nickel catalyst is dried by repeatedly stirring with dry ethanol and decanting. In the hydrogenation reactor, KF (1.53 g, 26.3 mmol), Ala-Pro (4.85 g, 25.0 mmol), and sieves (9.58 g) are suspended in ethanol (46 ml) and acetic acid (1.79 ml, 31.3 mmol), and the mixture is inerted with nitrogen. The Raney nickel (5.13 g) is added and the mixture is inerted. The ketoester (5.68 mL, 27.5 mmol) is added last, rinsing into the flask with ethanol (2.2 mL). The reactor is inerted by evacuating and refilling with nitrogen three times. The reactor is evacuated again and filled with hydrogen to 14 psia. (A mixture of hydrogen and nitrogen can be used to attain a higher total pressure with 1 atm hydrogen). The reaction is carried out at 22° C. for about 18 h. Note: The time from charging ketoester to beginning hydrogenation should be minimized to limit the dimerization of ketoester to hydroxyfuranone, a reaction which is accelerated by KF.

The catalyst is removed by filtration rinsing with ethanol. HPLC analysis of the filtrate shows a yield of enalapril (SSS isomer) of 8.13 g (86.5%). The yield of the RSS isomer is 0.46 g (4.9%).

| HPLC conditions: | |
|---|---|
| Column: | Merck LiChrosphere 60 RP-Select B 5 micron; 250 × 4.0 mm |
| Mobile phase: | acetonitrile/pH 3.0 buffer (made from 20 mM NaH$_2$PO$_4$, brought to pH with H$_3$PO$_4$) |
| Gradient: | a) 30/70 0–8 min |
| | b) linear increase to 50/50 over 8–14 min |
| | c) hold 50/50 14–28 min |
| Flow rate: | 1.2 ml/min |
| Temperature: | 70° C. |
| Detection: | UV 210 nm |

| Compound: | Retention Time: |
|---|---|
| Ala-Pro: | 1.57 min |
| Acetic acid: | 1.90 min |
| Enalapril (SSS isomer): | 6.5 min |
| RSS isomer: | 7.4 min |
| Hydroxyester: | 13.7 min |
| Diketopiperazine: | 15.0 min |
| Toluene: | 15.5 min |
| α-Ketoester: | 15–17 min broad |
| Hydroxyfuranone | 24.0 min |

What is claimed:

1. A process for the preparation of enalapril

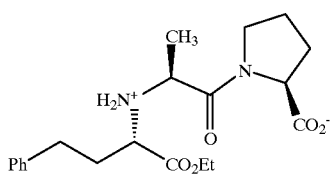

comprising reacting a dipeptide

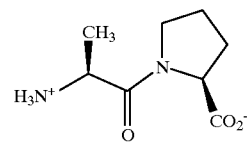

in ethanol, powdered sieves, one or more additives, an ethanol solution of catalyst, with an α-ketoester

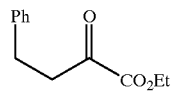

under hydrogen, while stirring, to produce the enalapril.

2. The process as recited in claim 1 wherein the catalyst is Ra-Ni, Pt/Al$_2$O$_3$, and Pd/Al$_2$O.

3. The process as recited in claim 2 wherein the additives are selected from: amino acid derivatives, carbohydrates, salts, organic acids, and Lewis acids.

4. The process as recited in claim 3 wherein one of the additives is a salt selected from: LiF, NaF, KF, CsF, LiCl, NaCl, KCl, LiBr, NaBr, KBr, NaI, tetraalkylammonium bromides, wherein alkyl is defined as C$_1$–C$_6$ alkyl.

5. The process as recited in claim 3 wherein one of the additives is an organic acid selected from: acetic acid, propionic acid, trifluoroacetic acid, citric acid, lactic acid, ascorbic acid, pyroglutamic acid, diphenylacetic acid, tartaric acid, indole-3-acetic acid, nicotinic acid, nipecotic acid, and picolinic acid.

6. The process as recited in claim 3 wherein two additives are used.

7. The process as recited in claim 6 wherein the catalyst is Ra-Ni.

8. The process as recited in claim 7 wherein the second additive is a salt.

9. The process as recited in claim 8 wherein the second additive is a salt selected from: LiF, NaF, KF, CsF, LiCl, NaCl, KCl, LiBr, NaBr, KBr, NaI, tetraalkylammonium bromides, wherein alkyl is defined as C$_1$–C$_6$ alkyl.

10. The process as recited in claim 9 wherein the two additives are: acetic acid (HOAc) and potassium fluoride (KF), or acetic acid (HOAc) and cesium fluoride (CsF).

11. The process as recited in claim 10 wherein about 2 psia to about 100 psia of hydrogen is used.

12. The process as recited in claim 11 wherein the reaction temperature is about 0° C. to about 40° C.

13. The process as recited in claim 12 wherein about 2 psia to about 54 psia of hydrogen is used.

14. The process as recited in claim 13 wherein the reaction temperature is about 15° C. to about 30° C.

15. The process as recited in claim 6 wherein the catalyst is Pt/Al$_2$O.

16. The process as recited in claim 15 wherein the second additive is a salt.

17. The process as recited in claim 16 wherein the second additive is a salt selected from: LiF, NaF, KF, CsF, LiCl, NaCl, KCl, LiBr, NaBr, KBr, NaI, tetraalkylammonium bromides, wherein alkyl is defined as C$_1$–C$_6$ alkyl.

18. The process as recited in claim 17 wherein the two additives are: acetic acid (HOAc) and sodium bromide (NaBr).

19. The process as recited in claim 18 wherein about 2 psia to about 100 psia of hydrogen is used.

20. The process as recited in claim 19 wherein the reaction temperature is about 0° C. to about 40° C.

21. The process as recited in claim 20 wherein about 2 psia to about 54 psia of hydrogen is used.

22. The process as recited in claim 21 wherein the reaction temperature is about 15° C. to about 30° C.

* * * * *

(12) REEXAMINATION CERTIFICATE (4658th)
United States Patent
Huffman et al.

(10) Number: US 6,025,500 C1
(45) Certificate Issued: Oct. 15, 2002

(54) STEREOSELECTIVE PROCESS FOR ENALAPRIL

(75) Inventors: Mark A. Huffman, Edgewater; Paul J. Reider, Westfield; Carl Leblond, Somerset; Yongkui Sun, Bridgewater, all of NJ (US)

(73) Assignee: Merck & Co., Inc., Rahway, NJ (US)

Reexamination Request:
No. 90/005,736, May 24, 2000

Reexamination Certificate for:
Patent No.: 6,025,500
Issued: Feb. 15, 2000
Appl. No.: 09/397,949
Filed: Sep. 17, 1999

(21) Appl. No.: 09/397,949

Related U.S. Application Data

(60) Provisional application No. 60/101,458, filed on Sep. 23, 1998.

(51) Int. Cl.[7] .................. C07D 207/08; C07D 207/16
(52) U.S. Cl. .................................................. 548/533

(56) References Cited

U.S. PATENT DOCUMENTS

| | | |
|---|---|---|
| 4,442,030 A | 4/1984 | Greenlee |
| 5,319,098 A | 6/1994 | Burbaum et al. |
| 5,387,696 A | 2/1995 | Kottenhahn et al. |
| 5,473,081 A | 12/1995 | Kobayashi et al. |
| 5,670,655 A | 9/1997 | Qin et al. |
| 5,707,991 A | 1/1998 | Capet et al. |
| 5,898,076 A | 4/1999 | Giselbrecht et al. |
| 5,962,696 A | 10/1999 | Tanner et al. |
| 5,977,380 A | 11/1999 | Yang et al. |

FOREIGN PATENT DOCUMENTS

| | | |
|---|---|---|
| EP | 0 523 449 | 1/1993 |
| PL | 162949 | 11/1990 |

OTHER PUBLICATIONS

Blacklock, T. J., et al, J. Org. Chem., vol. 53, pp. 836–844, 1988.

Wojciechowska, H., et al., Chem. ABS., vol. 122(15), ABS No. 188175, 1995 (Cumulative with PL 162949).

*Primary Examiner*—Robert W. Ramsuer

(57) ABSTRACT

The invention relates to an improved stereoselective heterogenous catalytic reductive amination between ethyl 2-oxo-4-phenylbutyrate and alanylproline using hydgrogen, a catalyst and one or more additives to produce the ACE inhibitor, enalapril.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, line 57–column 2, line 17:
A process for the preparation of enalapril

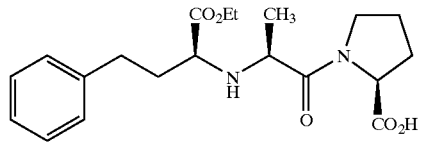

comprising reacting a dipeptide

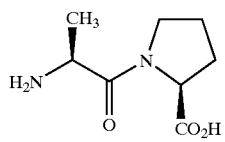

in ethanol, powdered sieves, one or more additives, a catalyst, with a α-ketoester

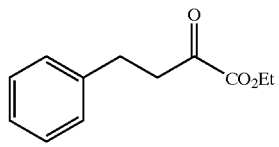

under hydrogen, while stirring, to produce the enalapril.

AS A RESULT OF REEXAMINATION, IT HAS BEEN DETERMINED THAT:

Claims 2–5 are cancelled.

Claims 1, 6 and 15 are determined to be patentable as amended.

Claims 7–14 and 16–22, dependent on an amended claim, are determined to be patentable.

1. A process for the preparation of enalapril

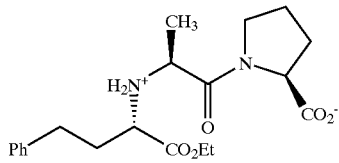

[comprising] *consisting essentially of* reacting a dipeptide

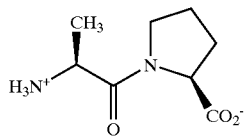

in ethanol, powdered sieves, one or more additives *selected from the group consisting of: carbohydrates, salts, Lewis acids, and organic acids, excluding amino acid derivatives, wherein at least one of the additives is the organic acid selected from: acetic acid, propionic acid, trifluoroacetic acid, citric acid, lactic acid, ascorbic acid, pyroglutamic acid, diphenylacetic acid, tartaric acid, indole-3-acetic acid, nicotinic acid, nipecotic acid, and picolinic acid*, an ethanol solution of catalyst, *wherein the catalyst is Ra-Ni, Pt/Al$_2$O$_3$, or Pd/Al$_2$O$_3$*, with an β-ketoester

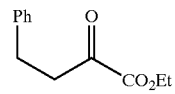

under hydrogen, while stirring, to produce the enalapril.

6. The process as recited in claim [3] *1* wherein two additives are used.

15. The process as recited in claim 6 wherein the catalyst is [Pt/Al$_2$O] *Pt/Al$_2$O$_3$*.

* * * * *